United States Patent [19]

Itoh

[11] Patent Number: 5,734,114
[45] Date of Patent: Mar. 31, 1998

[54] NOZZLE APPARATUS FOR SAMPLING AND DISPENSING SPECIMEN

[76] Inventor: Teruaki Itoh, 5-25, Kokaihonmachi, Kumamoto-shi, Kumamoto-ken 860, Japan

[21] Appl. No.: 705,973

[22] Filed: Aug. 30, 1996

[30] Foreign Application Priority Data

Aug. 31, 1995 [JP] Japan ................................. 7-223933
Jan. 11, 1996 [JP] Japan ................................. 8-003182

[51] Int. Cl.$^6$ ............................................. G01N 35/10
[52] U.S. Cl. .......................... 73/864.14; 73/863; 73/864; 73/864.11; 73/864.73
[58] Field of Search ................................. 604/19, 35, 68, 604/73, 104–107, 174, 264, 275, 278, 313, 315, 316, 902; 222/394; 277/34.3; 73/864.14

[56] References Cited

U.S. PATENT DOCUMENTS 4,747,316  5/1988  Rabinovich .
4,783,108  11/1988  Fukuyama et al. .
5,406,856  4/1995  Kühn .

FOREIGN PATENT DOCUMENTS 0 337 726  10/1989  European Pat. Off. .
0 547 503  6/1993  European Pat. Off. .
WO 91/16975  11/1991  WIPO .

*Primary Examiner*—Michael Buiz
*Assistant Examiner*—David O. Reip
*Attorney, Agent, or Firm*—Nixon & Vanderhye

[57] ABSTRACT

A nozzle apparatus for sampling-dispensing a specimen comprises a nozzle body and an annular elastic bag made of an elastic member and formed to cover the outer circumferential surface at the distal end portion of the nozzle body such that fluid such as air can be sealed in the inner space of the elastic bag. When a specimen sampling-dispensing tip is mounted to the nozzle apparatus, fluid is supplied into the elastic bag, with the distal end portion of the nozzle body kept inserted into a mounting section of the tip, so as to expand the elastic bag such that the outer circumferential surface of the bag is pressed against the inner circumferential surface of the mounting section of the tip so as to ensure a hermetic contact therebetween. When the tip is detached from the nozzle body, the fluid within the elastic bag is discharged so as to shrink the bag and, thus, to cause the outer circumferential surface of the bag to be moved away from the inner circumferential surface of the mounting section of the tip, thereby to move the distal end portion of the nozzle body from within the mounting section of the specimen sampling-dispensing tip.

4 Claims, 4 Drawing Sheets

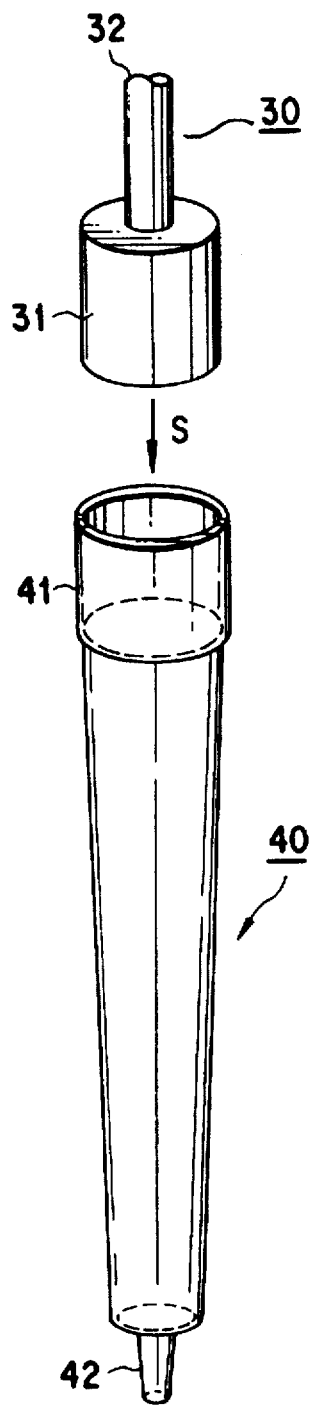
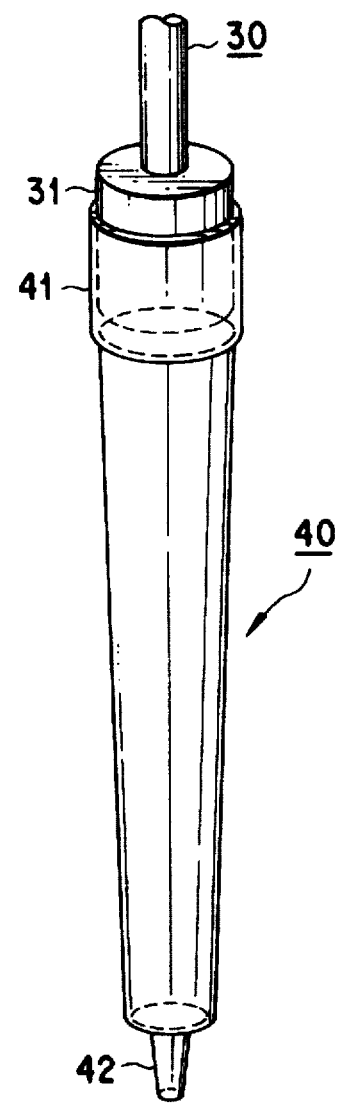
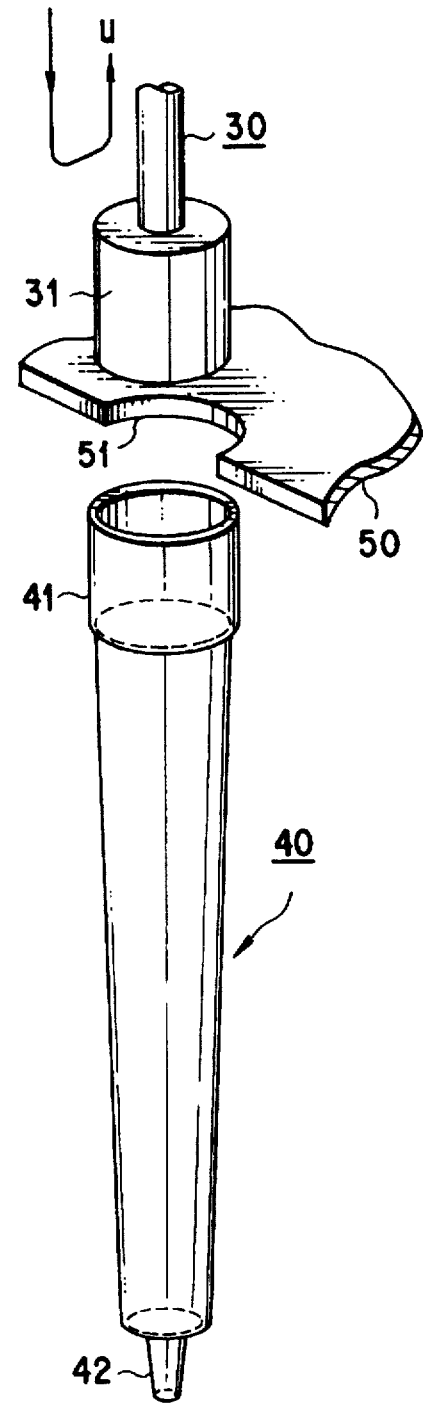
F I G. 6
(PRIOR ART)
F I G. 7
(PRIOR ART)
F I G. 8
(PRIOR ART)

NOZZLE APPARATUS FOR SAMPLING AND DISPENSING SPECIMEN

BACKGROUND OF THE INVENTION

1. Field of the Invention

The present invention relates to a nozzle apparatus for sampling and dispensing a specimen, said apparatus having a sampling-dispensing tip of throwaway type mounted to a distal end portion of a nozzle apparatus and being used for sampling a specimen such as blood housed in a specimen container such as a parent test tube and for dispensing the sampled specimen into a plurality of child test tubes depending on the purposes of the dispensation.

2. Description of the Related Art

FIGS. 6 to 8 collectively show the construction of a conventional nozzle apparatus for sampling-dispensing a specimen, in which FIG. 6 is an oblique view showing the state before mounting of a sampling-dispensing tip 40 to a nozzle apparatus, FIG. 7 is an oblique view showing the state after mounting of the tip 40 to the nozzle apparatus, and FIG. 8 is an oblique view showing the state immediately after detachment of the tip 40 from the nozzle apparatus.

As shown in FIG. 6, the conventional nozzle apparatus for sampling-dispensing a specimen comprises the nozzle body 30 and a stopper member 31. The stopper member 31 made of rubber, cork or another material having a slight elasticity is mounted to a distal end portion of the nozzle body 30. The stopper member 31 is sized to be exactly fitted into the opening of a mounting section 41 of the throwaway type sampling-dispensing tip 40. A proximal end portion 32, which extends upward in the drawing, of the nozzle body 30 is connected to a gateway of a suction-discharge apparatus (not shown). The entire region of the nozzle apparatus is held movable in both vertical and horizontal directions by a moving mechanism (not shown).

The sampling-dispensing tip 40 consists essentially of a tapered tubular body made of, for example, a resin. A tip portion 42 of a small diameter, which is adapted for sucking a specimen such as blood into the tip 40 and for discharging the sucked specimen out of the tip 40, is mounted to the distal end portion of the tip 40.

When the nozzle body 30 is moved by the moving mechanism to a predetermined position relative to the sampling-dispensing tip 40 under a waiting state in which the mounting section 41 forms an upper portion and, then, inserted from above as denoted by an arrow S into the mounting section 41 of the tip 40, the stopper member 31 is engaged with the mounting section 41 so as to form an integral structure, as shown in FIG. 7.

Where the stopper member 31 is pressed into the mounting section 41 of the sampling-dispensing tip 40, the nozzle apparatus and the tip 40 are made mechanically integral and hermetically joined to each other, as apparent from FIG. 7. As a result, the nozzle apparatus is enabled to perform its function of sampling-dispensing a specimen via the throwaway type sampling-dispensing tip 40 for the specimen.

FIG. 8 shows that the tip 40 used for sampling-dispensing the specimen is detached for disposal from the stopper member 31 of the nozzle apparatus.

A reference numeral 50 in FIG. 8 denotes a plate used as a tool for detaching the tip 40. It is seen that a semi-circular recess 51 is formed in one side of the plate 50. The radius of the recess 51 is larger than the radius of the stopper member 31 and smaller than the cylindrical mounting section 41 of the sampling-dispensing tip 40.

In detaching the tip 40 from the stopper member 31 of the nozzle apparatus, the nozzle apparatus is moved by the moving mechanism as denoted by an arrow U in FIG. 8 such that the stopper member 31 passes upward through the semi-circular recess 51. In this step, an edge of the mounting section 41 of the sampling-dispensing tip 40 is caught by the semi-circular recess 51, resulting in failure for the mounting section 41 to pass through the recess 51, though the stopper member 31 passes smoothly through the recess 51. Therefore, if the nozzle apparatus is further moved upward, the tip 40 is detached from the stopper member 31 so as to drop into a waste container (not shown).

As described above, the conventional nozzle apparatus for sampling-dispensing a specimen comprises the nozzle body 30 and the columnar stopper member 31 made of a relatively hard material such as rubber or cork, which certainly has a slight elasticity, and mounted to the distal end portion of the nozzle body 30. In the conventional apparatus, the stopper member 31 is pressed into the opening in the mounting section 41 of the sampling-dispensing tip 40 for the specimen. What should be noted is that, if the mounting section 41 of the tip 40 is deformed into, for example, an elliptical shape, the outer circumferential surface of the stopper member 31 fails to fit the inner circumferential surface of the mounting section 41. It follows that an air-tightness cannot be maintained between the stopper member 31 and the mounting section 41.

Further, where an impact-like vibration has taken place on the side of the nozzle body 30, the vibration is transmitted substantially directly to the tip 40 because the stopper member 31 interposed between the nozzle body 30 and the tip 40 is made of a relatively hard material. The impact-like vibration transmitted to the sampling-dispensing tip 40 tends to cause the specimen sucked into the tip 40 to drip out of the tip 40. In view of the dripping problem, it was customary in the past to take measures such as a soft-start control and a soft-stop control so as to prevent an impact-like vibration from taking place on the side of the nozzle body 30. However, these measures caused the sampling-dispensing speed of the specimen to be lowered, with the result that it was impossible to perform the sampling-dispensing operation efficiently.

Still further, it was necessary to use a special tool such as the plate 50 for detaching the sampling-dispensing tip 40 from the nozzle apparatus. As a result, the sampling-dispensing apparatus was rendered complex in construction and bulky. In addition, use of the plate 50 caused the tip detaching efficiency to be lowered, leading to reduction in the efficiency of the sampling-dispensing efficiency of the specimen.

SUMMARY OF THE INVENTION

An object of the present invention is to provide a nozzle apparatus of types (a) to (c) given below for sampling-dispensing a specimen:

(a) A nozzle apparatus for sampling-dispensing a specimen, which permits a sampling-dispensing tip for a specimen to be mounted to and detached from the nozzle body with safety, without fail and at a high speed, even if the mounting section of the sampling-dispensing tip is somewhat deformed.

(b) A nozzle apparatus for sampling-dispensing a specimen, which permits preventing an impact-like vibration taking place on the side of the nozzle body from being transmitted substantially directly to the sampling-dispensing tip so as to prevent the specimen within the tip from being dripped out of the tip, and also permits increasing the speed of the sampling-dispensing operation of the specimen.

(c) A nozzle apparatus for sampling-dispensing a specimen, which permits eliminating a special tool for detaching a sampling-dispensing tip from the nozzle body so as to simplify the construction of the nozzle apparatus and to improve the tip detaching efficiency.

A nozzle apparatus having any of constructions (1) to (2) given below is adapted for achieving the particular object of the present invention:

(1) A nozzle apparatus for sampling-dispensing a specimen, comprising:

a nozzle body for sampling-dispensing a specimen by sucking-discharging the specimen;

an annular elastic bag made of an elastic member and mounted to surround the outer circumferential surface at a distal end portion of the nozzle body such that fluid can be sealed therein;

means for mounting a sampling-dispensing tip for a specimen by supplying fluid into the elastic bag so as to expand the bag; and means for detaching the sampling-dispensing tip by discharging the fluid from within the elastic bag so as to shrink the bag.

(2) A nozzle apparatus for sampling-dispensing a specimen, comprising:

a nozzle body having a proximal end portion connected to a gateway of a suction-discharge apparatus and a distal end portion removably inserted into a mounting section of a sampling-dispensing tip for a specimen;

an annular elastic bag made of an elastic member such as rubber and mounted to surround the outer circumferential surface at a distal end portion of the nozzle body such that the outer circumferential surface of the bag can be hermetically brought into contact with the inner circumferential surface of a mounting section of a specimen sampling-dispensing tip, and that fluid such as air can be sealed in the bag; and means for expanding-shrinking the elastic bag by supplying fluid into the bag so as to expand the bag in at least a radial direction and discharging the fluid from within the bag so as to shrink the bag;

wherein;

fluid is supplied into the elastic bag in the step of mounting the specimen sampling-dispensing tip, with the distal end portion of the nozzle body held inserted into the mounting section of the tip, so as to expand the bag in at least a radial direction such that the outer circumferential surface of the bag is hermetically brought into contact with the inner circumferential surface of the mounting section of the tip; and the fluid is discharged from within the elastic bag in the step of detaching the tip so as to shrink the bag such that the outer circumferential surface of the bag is moved away from the inner circumferential surface of the mounting section of the sampling-dispensing tip, thereby removing the distal end portion of the nozzle body from within the mounting section of the tip.

The nozzle apparatus for sampling-dispensing a specimen, which is set forth in any of items (1) and (2) described above, comprises a first fluid passageway for sucking-discharging a specimen, said first fluid passageway being formed along the axis of the nozzle body, and a second fluid passageway coaxial with the first fluid passageway and used for supplying-exhausting fluid into and out of the elastic bag.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 6 is an oblique view showing the construction of a conventional nozzle apparatus for sampling-dispensing a specimen, which covers the state before mounting of a sampling-dispensing tip to a nozzle apparatus;

FIG. 7 is an oblique view showing the construction of a conventional nozzle apparatus for sampling-dispensing a specimen, which covers the state after mounting of a sampling-dispensing tip to a nozzle apparatus; and FIG. 8 is an oblique view showing the construction of a conventional nozzle apparatus for sampling-dispensing a specimen, which covers the state immediately after detachment of a sampling-dispensing tip from a nozzle apparatus.

DETAILED DESCRIPTION OF THE PREFERRED EMBODIMENTS (First Embodiment)

Figure 1:
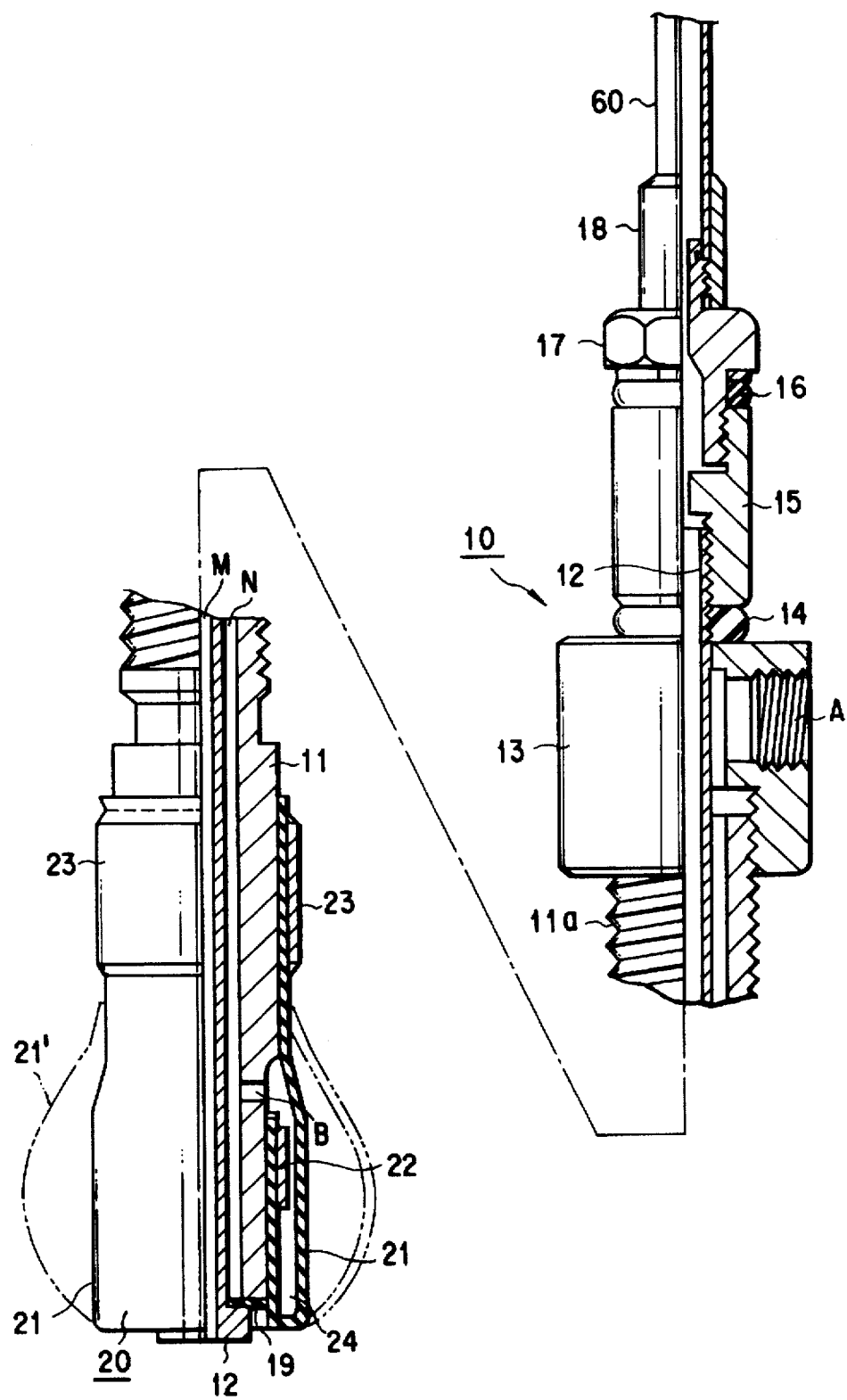
FIG. 1 is a side view, the right-hand half region being broken away, showing the construction of a nozzle apparatus for sampling-dispensing a specimen according to a first embodiment of the present invention.

FIG. 1 is a side view, the right-hand half region being broken away, showing the construction of a nozzle apparatus for sampling-dispensing a specimen according to a first embodiment of the present invention. As shown in FIG. 1, the nozzle apparatus comprises a nozzle body 10 and an annular elastic bag 20 made of an elastic member and surrounding the outer circumferential surface in a distal end portion of the nozzle body 10. Fluid, i.e., air in this embodiment, can be sealed in the hollow portion of the elastic bag 20.

The nozzle body 10 comprises a cylindrical base body 11 having a pipe 12 formed within the inner space thereof. The pipe 12 is coaxial with and is positioned a predetermined distance apart from the cylindrical base body 11. To be more specific, a predetermined space is provided between the outer surface of the pipe 12 and the inner surface of the cylindrical base body 11. An externally threaded portion 11a is formed in a proximal end portion (upper side in the drawing) of the cylindrical base body 11 for screw-engagement with an air lead member 13. An air flow port A for introducing-exhausting the air from outside-inside the nozzle body 10 in the steps of mounting-detaching a tip for sampling-dispensing a specimen is formed in the air lead member 13. It is seen that a rubber packing 14 is fitted over the outer circumferential surface of the pipe 12 projecting upward from the proximal end portion of the air lead member 13. Further, a cylindrical connector member 15 is screw-engaged with the pipe 12. Still further, a lock member 17 is screw-engaged with an upper end portion of the connector member 15 with another rubber packing 16 interposed therebetween. One end of a pipe 60 is connected via a connector member 18 to the upper end of the lock member 17, with the other end being connected to a suction-discharge port of a suction-discharge apparatus (not shown).

A rubber packing 19 is interposed in the distal end portion between the cylindrical base body 11 and the pipe 12 so as to achieve a hermetic sealing between the cylindrical base body 11 and the pipe 12 in the distal end portion of the apparatus.

The inner space of the pipe 12, which extends along the axis of the cylindrical base body 11, is used as a passageway M for sucking/discharging a specimen. Likewise, the annular space formed between the outer surface of the pipe 12 and the inner surface of the cylindrical base body 11 is used as an air passageway N through which the air is introduced into and discharged from the elastic bag 20. As apparent from the drawing, these passageways M and N are coaxial.

The elastic bag 20, which is made of an elastic member 21 such as rubber and is shaped like an annular bag, is mounted to surround the outer circumferential surface in the distal end portion of the nozzle body 10.

The elastic bag 20 is prepared as follows. In the first step, one end portion of the cylindrical elastic member 21 is fitted with a small diameter portion on the side of the distal end of the cylindrical base body 11, followed by fastening the fitted portion with a fastening ring 22 so as to fix said one end portion. Then, the cylindrical elastic member 21 is reversed or folded upward, and the reversed other end portion is fitted with a large diameter portion on the side of the proximal end of the cylindrical base body 11, followed by fastening the fitted portion with another fastening ring 23 so as to fix said other end portion and, thus, to form the annular elastic bag 20. When the annular elastic bag 20 is expanded by blowing air into an inner space 24 of the bag 20, the outer circumferential surface of the bag 20 is brought into contact with the inner circumferential surface of the mounting section included in the specimen sampling-dispensing tip 40 shown in FIGS. 2 and 3. Incidentally, the air is blown into the inner space 24 of the bag 20 through an air hole B extending through the circumferential wall of the cylindrical base body 11. FIG. 1 shows that, upon sealing of the air, the elastic member 21 of the elastic bag 20 is expanded as denoted by a reference numeral 21'.

Figure 2:
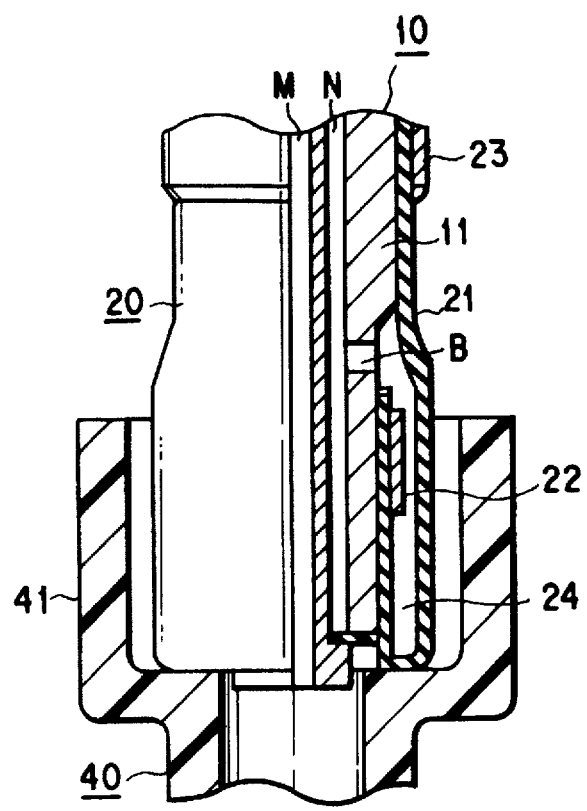
FIG. 2 shows how to use the nozzle apparatus according to the first embodiment of the present invention as well as the function performed by the nozzle apparatus, the nozzle apparatus being under the state that fluid is not sealed therein.
Figure 3:
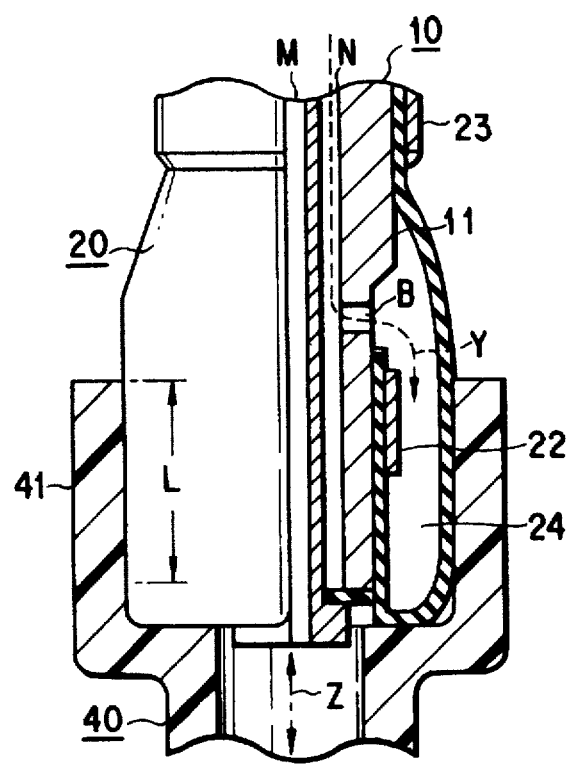
FIG. 3 shows how to use the nozzle apparatus according to the first embodiment of the present invention as well as the function performed by the nozzle apparatus, the nozzle apparatus being under the state that fluid is sealed therein.

FIGS. 2 and 3 collectively show how to use the nozzle apparatus for sampling-dispensing a specimen, which is constructed as described above. In the step of mounting a sampling-dispensing tip, the elastic bag 20 mounted to the distal end portion of the nozzle body 10 is inserted into the opening in the mounting section 41 of the tip 40, as shown in FIG. 2.

If the air is introduced under this condition through the air flow port A, the air flows through the air passageway N and, then, through the air hole B so as to be sealed in the inner space 24 of the elastic bag 20. As a result, the elastic member 21 of the bag 20 is expanded so as to cause the outer circumferential surface of the bag 20 to be brought into a hermetic contact with the inner circumferential surface of the mounting section 41 included in the sampling-dispensing tip 40 over a depth L, as shown in FIG. 3. In short, the nozzle body 10 is hermetically coupled with the tip 40 to form an integral body.

The resultant integral body is moved by a moving mechanism (not shown) to a predetermined position, followed by operating the suction-discharge apparatus at the predetermined position. As a result, the air suction-discharge function is performed through the pipe 60 and the passageway M extending along the axis of the nozzle body 10, as shown by an arrow Z. In this fashion, the throwaway type specimen sampling-dispensing tip 40 is enabled to suck-dispense the specimen.

When the sampling-dispensing tip 40 is detached from the nozzle body 10 after completion of the sampling-dispensing operation, the air is discharged out of the elastic bag 20 via the process opposite to that in the step of supplying the air. As a result, the elastic bag 20 is shrunk so as to cause the outer circumferential surface of the elastic member 21 to be moved away from the inner circumferential surface in the mounting section 41 of the sampling-dispensing tip 40, as shown in FIG. 2. It follows that the tip 40 is detached from the distal end portion of the nozzle body 10.

(Second Embodiment)

Figure 4:
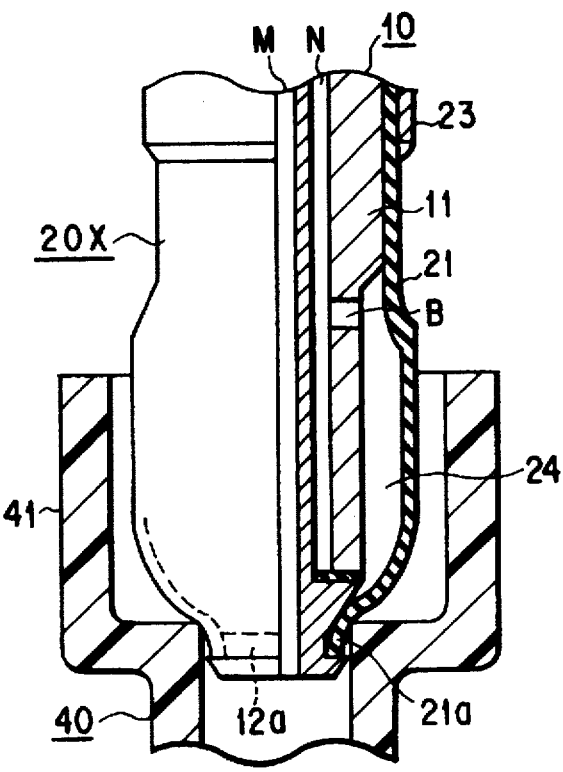
FIG. 4 shows how to use the nozzle apparatus according to a second embodiment of the present invention as well as the function performed by the nozzle apparatus, the nozzle apparatus being under the state that fluid is not sealed therein.
Figure 5:
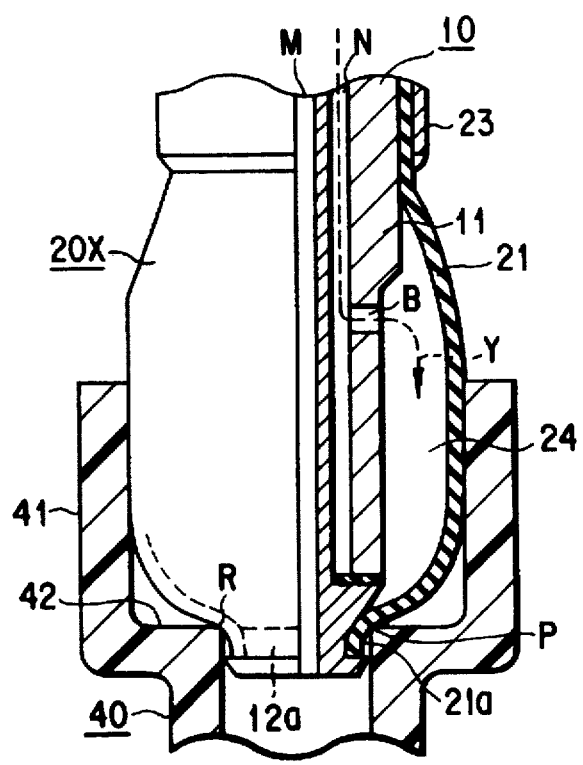
FIG. 5 shows how to use the nozzle apparatus according to the second embodiment of the present invention as well as the function performed by the nozzle apparatus, the nozzle apparatus being under the state that fluid is sealed therein.

FIGS. 4 and 5 collectively show the construction of a nozzle apparatus for sampling-dispensing a specimen according to a second embodiment of the present invention. The nozzle apparatus for the second embodiment differs from that for the first embodiment in that, in the second embodiment, the distal end portion (lower end portion in the drawing) of the elastic member 21 forming an elastic bag 20X is fixed to the distal end portion of the pipe 12. To be more specific, the small diameter portion (lower end portion in the drawing) 21a at the tip of the tapered tubular elastic member 21 is not folded upward for fixing to the outer circumferential surface of the cylindrical base body 11 but is engaged with an annular recess 12a formed in the outer circumferential surface at the distal end portion of the pipe 12.

The second embodiment of the construction described above is advantageous over the first embodiment, in which the distal end portion of the elastic member 21 is folded upward for fixing to the outer circumferential surface of the cylindrical base body 11, in that the elastic member 21 can be fixed easily, that the raw material cost can be lowered, and that the manufacturing cost of the nozzle apparatus can be lowered.

If the air is supplied into the inner space 24 of the elastic bag 20X under the condition as shown in FIG. 4, the bag 20X is expanded as shown in FIG. 5. In this step, an outer circumferential portion P at the small diameter portion 21a of the elastic member 21 is allowed to abut strongly against a corner portion R in a stepped portion 42 of the tip 40. As a result, the small diameter portion 21a at the tip of the elastic member 21 is prevented from being disengaged from the annular recess 12a. It follows that the elastic bag 20X, which has a very simple construction, permits ensuring a quite satisfactory air-tightness between the small diameter portion 21a at the tip of the elastic member 21 and the annular recess 12a formed in the outer circumferential surface of the pipe 12. Naturally, the elastic bag 20X performs a satisfactory function as required.

(Modifications)

In the embodiments described above, air is sealed in the elastic bag 20 or 20X. However, another fluid such as an inert gas or water can be sealed in the elastic bag, with satisfactory results. Also, the elastic member 21 is formed of rubber in the embodiments described above. However, another material such as a soft plastic material can also be used for forming the elastic member 21.

(Merits of the Embodiments)

[1] As described above, the nozzle apparatus for sampling-dispensing a specimen, which has the first construction specified in the present invention, comprises a nozzle body 10 for sampling-dispensing a specimen by sucking-discharging the specimen, an annular elastic bag 20 made of an elastic member 21 and mounted to surround the outer circumferential surface at a distal end portion of the nozzle body 10 such that fluid can be sealed in an inner space 24 thereof, means for mounting a specimen sampling-dispensing tip 40 by supplying fluid into the elastic bag 20 so as to expand the bag 20, and means for detaching the sampling-dispensing tip 40 by discharging the fluid from within the elastic bag 20 so as to shrink the bag 20.

According to the nozzle apparatus having the first construction [1] described above, the outer circumferential surface of the elastic bag 20 is kept pressed stably to fit the shape in the inner circumferential surface in the mounting section 41 of the sampling-dispensing tip 40, even if the mounting section 41 is deformed into, for example, an elliptical shape. As a result, no clearance is generated between the nozzle body 10 and the sampling-dispensing tip 40 so as to ensure air-tightness sufficiently.

Further, the bag 20 is so elastic that an impact-like vibration taking place on the side of the nozzle body 10 can be absorbed by the elastic bag 20, making it possible to prevent the impact-like vibration from being transmitted substantially directly to the specimen sampling-dispensing tip 40. Naturally, even if some impact-like vibration has taken place on the side of the nozzle body 10 during the specimen sampling-dispensing operation, the specimen housed in the sampling-dispensing tip 40 is quite unlikely to drip out of the tip 40. As a result, the nozzle body 10 can be moved promptly by the moving mechanism, leading to improvement in the speed of the sampling-dispensing operation.

It should also be noted that the expansion rate of the elastic bag 20 is incomparably higher than the abrasion rate on the outer circumferential surface of the elastic bag 20. It follows that, even if the elastic member 21 of the elastic bag 20 is abraded to some extent during use of the nozzle apparatus over a long period of time, the bonding strength between the elastic bag 20 and the sampling-dispensing tip 40 is not lowered, making it possible to maintain a stable tip-mounting function over a long period of time.

Still further, the sampling-dispensing tip 40 can be detached from the nozzle body 10 by simply shrinking the elastic bag 20, making it quite unnecessary to use the special detaching tool used in the conventional apparatus. It follows that the construction of the nozzle apparatus can be markedly simplified.

[2] The nozzle apparatus for sampling-dispensing a specimen, which has the second construction specified in the present invention, comprises a nozzle body 10 having a proximal end portion connected to a gateway a suction-discharge apparatus and a distal end portion removably inserted into a mounting section 41 of a specimen sampling-dispensing tip 40, an annular elastic bag 20 made of an elastic member 21 such as rubber and mounted to surround the outer circumferential surface at a distal end portion of the nozzle body 10 such that the outer circumferential surface of the bag 20 can be brought into tight contact with the inner circumferential surface of the mounting section 41 of the specimen sampling-dispensing tip 40, and that fluid such as air can be sealed in the inner space 24 of the bag 20, and means for expanding-shrinking the elastic bag 20 by supplying fluid into the bag 20 so as to expand the bag 20 in at least a radial direction and discharging the fluid from within the bag 20 so as to shrink the bag, wherein, fluid is supplied into the elastic bag 20 in the step of mounting the tip 40, with the distal end portion of the nozzle body 10 held inserted into the mounting section 41 of the tip 40, so as to expand the bag 20 in at least a radial direction such that the outer circumferential surface of the bag 20 is hermetically brought into contact with the inner circumferential surface of the mounting section 41 of the tip 40, and the fluid is discharged from within the elastic bag 20 in the step of detaching the tip so as to shrink the bag 20 such that the outer circumferential surface of the bag 20 is moved away from the inner circumferential surface of the mounting section 41 of the sampling-dispensing tip 40, thereby removing the distal end portion of the nozzle body 10 from within the mounting section 41 of the tip 40.

The nozzle apparatus having the second construction [2] described above produces the function and effect similar to those produced by the nozzle apparatus having the first construction [1] described previously. In addition, the nozzle apparatus having the second construction [2] is defined more clearly in construction, making the apparatus easier to be worked, compared with the apparatus having the first construction [1].

[3] The nozzle apparatus for sampling-dispensing a specimen, which has any of constructions [1] and [2] described above, comprises a first fluid passageway M for sucking-discharging a specimen, said passageway M being formed along the axis of the nozzle body 10, and a second fluid passageway N for supplying-exhausting fluid into and out of an elastic bag 20, said passageway N being positioned outside and coaxial with the first fluid passageway M.

According to the nozzle apparatus having the third construction [3] given above, the second fluid passageway N for supplying-exhausting fluid into and out of an elastic bag 20 is formed outside and coaxial with the first fluid passageway M for sucking-discharging a specimen. As a result, the second fluid passageway N permits fluid to flow in a sufficiently large amount and with a low flow resistance. Also, the space occupied by the second fluid passageway N is relatively small, making it possible to render the nozzle apparatus compact.

[4] The nozzle apparatus for sampling-dispensing a specimen, which has any of constructions [1] and [2] described above, comprises the elastic bag 20 prepared by the steps of:

allowing one end portion of the cylindrical elastic member 21 to be fitted with a small diameter portion on the side of the distal end of the cylindrical base body 11, followed by fastening the fitted portion with a fastening ring 22 so as to fix said one end portion; and reversing to fold upward the cylindrical elastic member 21, and allowing the reversed other end portion to be fitted with a large diameter portion on the side of the proximal end of the cylindrical base body 11, followed by fastening the fitted portion with another fastening ring 23 so as to fix said other end portion and, thus, to form the annular elastic bag 20.

According to the nozzle apparatus having the fourth construction [4] given above, the annular elastic bag 20 can be prepared without difficulty by using the elastic member 21 of a simple shape.

[5] The nozzle apparatus for sampling-dispensing a specimen, which has any of constructions [1] and [2] described above, comprises the annular elastic bag 20X prepared by allowing the tapered small diameter portion 21a at the distal end of the tubular elastic member 21 to be engaged with an annular recess 12a formed on the outer circumferential surface of the pipe 12.

The nozzle apparatus having the fifth construction [5] described above is advantageous over the case where the tip portion of the elastic member 21 is folded upward for fixing to the outer circumferential surface of the cylindrical base body 11, in that the elastic member 21 can be fixed easily, that the raw material cost can be lowered, and that the manufacturing cost of the nozzle apparatus can be lowered.

What is claimed is:

1. A nozzle apparatus for sampling-dispensing a specimen, comprising:

a nozzle body for sampling-dispensing a specimen by sucking-discharging the specimen, said body including an outer circumferential surface at a distal end portion of said nozzle body;

an annular elastic bag made of an elastic member and mounted to surround said outer circumferential surface such that fluid can be disposed and sealed within said elastic bag;

means for mounting a sampling-dispensing tip for a specimen by supplying fluid into the elastic bag so as to expand the bag;

means for detaching the sampling-dispensing tip by exhausting the fluid from within the elastic bag so as to collapse the bag;

said elastic bag having a small diameter end portion disposed about the distal end portion of said nozzle body, a fastening ring about said small diameter end portion to fix said small diameter end portion to said distal end portion of said nozzle body; and said elastic bag having a portion reverse-folded to overlie said small diameter end portion terminating in a large diameter end portion overlying a large diameter portion of said nozzle body, and a second fastening ring about said large diameter end portion to fix said large diameter end portion of said elastic bag to said large diameter portion of said nozzle body to form an annular elastic bag.

2. A nozzle apparatus according to claim 1 wherein said elastic bag is formed of rubber.

3. A nozzle apparatus for sampling-dispensing a specimen, comprising:

a nozzle body having a proximal end portion connected to a gateway of a suction-discharge apparatus and having a distal end portion for removable insertion into a mounting section of a sampling-dispensing tip for a specimen, said body including an outer circumferential surface at a distal end portion of said nozzle body;

an annular elastic bag formed of an elastic member and mounted to surround said outer circumferential surface such that fluid can be disposed within said elastic bag and the outer circumferential surface of the bag can be hermetically sealed in contact with an inner circumferential surface of a mounting section of a sampling-dispensing tip of the specimen in response to disposing fluid in the bag;

means for expanding-collapsing the elastic bag by supplying fluid into the bag so as to expand the bag in at least a radial direction and exhausting the fluid from within the bag so as to collapse the bag, said elastic bag having a small diameter end portion disposed about the distal end portion of said nozzle body, and a fastening ring about said small diameter end portion to fix said small diameter end portion to said distal end portion of said nozzle body; and said elastic bag having a portion reverse-folded to overlie said small diameter end portion terminating in a large diameter end portion overlying a large diameter portion of said nozzle body, and a second fastening ring about said large diameter end portion to fix said large diameter end portion of said elastic bag to said large diameter portion of said nozzle body to form an annular elastic bag.

4. The nozzle apparatus according to claim 3 wherein said elastic bag is formed of rubber.

* * * * *